United States Patent
Tiwari et al.

(10) Patent No.: US 7,622,478 B2
(45) Date of Patent: *Nov. 24, 2009

(54) 1-NITROACRIDINE/TUMOR INHIBITOR COMPOSITIONS

(76) Inventors: Raj Tiwari, 81-50 251 St., Bellrose, NY (US) 11426; Daniel Miller, 6 Fox Meadow Rd., Scarsdale, NY (US) 10583; Jerzy Kazimierz Konopa, Bitwy pod Lenino St. 40, Gdansk (PL) 80-809; Barbara Wysocka-Skrzela, Szeroka St. 15 m., Gdansk (PL) 80-835

(*) Notice: Subject to any disclaimer, the term of this patent is extended or adjusted under 35 U.S.C. 154(b) by 1337 days.

This patent is subject to a terminal disclaimer.

(21) Appl. No.: 09/789,496

(22) Filed: Feb. 16, 2001

(65) Prior Publication Data

US 2002/0037831 A1    Mar. 28, 2002

Related U.S. Application Data

(60) Provisional application No. 60/183,529, filed on Feb. 18, 2000.

(51) Int. Cl.
*A61K 31/473* (2006.01)
*C07D 219/10* (2006.01)
*C07D 219/12* (2006.01)

(52) U.S. Cl. .................... 514/297; 546/105
(58) Field of Classification Search .......... 514/297, 514/2

See application file for complete search history.

(56) References Cited

U.S. PATENT DOCUMENTS

| | | | | |
|---|---|---|---|---|
| 3,694,447 | A | 9/1972 | Pagano et al. | 260/279 |
| 4,139,531 | A | 2/1979 | Ledóchowski et al. | 546/106 |
| 4,603,125 | A | 7/1986 | Atwell et al. | 514/80 |
| 4,985,436 | A | 1/1991 | Pettit et al. | 514/287 |
| 4,996,237 | A | 2/1991 | Pettit et al. | 514/720 |
| 5,529,989 | A | 6/1996 | Pettit et al. | 514/287 |
| 5,561,122 | A | 10/1996 | Pettit et al. | 514/130 |
| 5,604,237 | A | 2/1997 | Dumaitre et al. | 514/297 |
| 5,639,725 | A * | 6/1997 | O'Reilly et al. | 514/12 |
| 5,696,131 | A | 12/1997 | Baguley et al. | 514/297 |
| 5,759,514 | A | 6/1998 | Mattes et al. | 424/1.65 |
| 5,891,864 | A | 4/1999 | Han et al. | 514/45 |
| 6,326,390 | B1 * | 12/2001 | Leung et al. | 514/383 |
| 6,538,038 | B1 * | 3/2003 | Pero et al. | 514/731 |

FOREIGN PATENT DOCUMENTS

| | | | |
|---|---|---|---|
| EP | 038 572 | 10/1980 | 219/10 |
| EP | 038 572 | * 10/1981 | |
| JP | 05331070 | 2/1993 | |
| WO | WO 99/16889 | * 4/1999 | |
| WO | WO99/34788 | 7/1999 | |
| WO | 99/58126 | * 11/1999 | |

OTHER PUBLICATIONS

Battegay (Journal of Molecular Medicine, 1995, vol. 73, pp. 333-346).*
Wilson et al (Journal of Medicinal Chamistry, 1989, vol. 32, pp. 23-30).*
Denny et al (Journal of Medicinal Chemistry, 1990, vol. 33, pp. 1288-1295).*
Shalinsky et al (Ann NY Acad Sci, 1999, vol. 878, pp. 236-270).*
Grosios et al (British Journal of Cancer, 1999, vol. 81, pp.1318-1327).*
Colleoni et al (American Journal of Clinical Oncology: Cancer Clinical Trials, (Aug. 1997) vol. 20, No. 4, pp. 383-386.*
Drug Facts and Comparisons (1999, Cada et al, Ed, p. 3283).*
abstract of Tew et al (Pharmacology and Experimental Therapeutics, 1992, vol. 56, pp. 323-339).*
Gately, 1997, Proc. Natl. Acad. Sic. USA 94:10868-10872.
Lee et al., 1996, J. Med. Chem, 39:2508-2517.
Mazerska et al., 1990, Arzneim.-Forsch./Drug Res. 40 (I), 4, 472-477.

* cited by examiner

*Primary Examiner*—Karen A Canella
(74) *Attorney, Agent, or Firm*—Cheryl H. Agris

(57) ABSTRACT

The invention is directed to 1-nitroacridine derivative(s)/tumor inhibitor(s) compositions as well as methods for using said compositions for inhibiting or preventing tumor growth, particularly, prostate cancer cell growth and metastases.

21 Claims, 3 Drawing Sheets

1-NITROACRIDINE/TUMOR INHIBITOR COMPOSITIONS

PRIORITY CLAIM

This application claims priority from provisional application Ser. No. 60/183,529, filed Feb. 18, 2000, under 35 U.S.C. §119 (e), the contents of which are incorporated herein by reference.

FIELD OF THE INVENTION

The invention is directed to using 1-nitroacridine derivative(s) and tumor inhibitor(s) for inhibiting or preventing tumor growth, particularly, prostate cancer tumor cell growth and metastases, as well as compositions comprising 1-nitroacridine derivative(s) and tumor inhibitor(s). In particular, the tumor inhibitor(s) may be one or more antiangiogenic agents.

BACKGROUND OF THE INVENTION

Prostate Cancer

Prostate cancer is the most common cancer in males over sixty in developed countries. Current estimates of new prostate cancer cases in North America are about 300,000 per year, of which approximately 40,000 will succumb to the disease. The etiology of prostate cancer is still not well understood but progression of benign hyperplasia to overt cancer requires co-ordinate changes in cell cycle and apoptosis and deregulation of negative growth regulating factors. Primary prostate cancer is curable by radical prostatectomy but the metastatic disease is refractory to most common forms of therapy.

Most deaths from prostate cancer, however, are due to metastatic disease that, in general, does not respond with good curative rates, to chemotherapy or radiation. Hormonal depletion either by physical or chemical castration by the use of gonadotrophin releasing hormone analogues, exogenous estrogens, antiandrogens, progestational agents or adrenal enzyme synthesis inhibitors such as ketoconazole and aminoglutethimide has been for long the major mode of treatment for prostate cancer. Since several different organs such as the hypothalamus, pituitary, adrenal gland, testes and the prostate are involved in modulating the biochemical effects of androgens, removal of the testis removes only 40% of the total secretory hormone and as such chemical anti-hormone therapy is the preferred mode of treatment. The major drawback, apart from the toxicity side effects, is the generation of highly aggressive hormone independent cells that are refractory to anti-hormone therapy. Treatment modalities that can target both hormone sensitive as well as hormone insensitive cells are likely to have greater success and is one of the major challenges in the therapy of prostate cancer.

Other classes of anti-prostate cancer drugs are currently in use (reviewed in Osterlink et al., in Cancer: Principles and Practice of Oncology, DeVita, V. T., Hellman, S., Rosenberg, S. A., Lippincott-Raven, 1997, pp. 1322-1375). Some examples include growth factor inhibitors such as suramin or estramustine that affects microtubule assembly and affects nuclear matrix, a key determinant of chromatin structure and nuclear shape. Reports on the efficacy of suramin, a compound that affects binding of growth factor with its receptor and adrenal steroidogenesis is mixed and the major drawback in its use either singly or in combination with hydrocortisone seems to exhibit toxicities ranging from myelopathy, vortex keratopathy and coagulopathy. Vinca alkaloids that also target the microtubule assembly, vinblastine and navelbine, have shown modest activities whereas cytoskeletal disrupting agents etoposide and paciltaxel that do not show much activity as single agents but have been to shown to synergize with estramustine. Other combination therapies currently being evaluated include cyclophosphamide plus GM-CSF and ketoconazole plus doxorubicin.

Therapeutic attempts have also been made with mitoxantrone. Mitoxantrone has modest activity alone in patients with advanced prostate cancer but can provide significant palliation when combined with prednisone with respect to pain relief and quality of life end point (Wiseman, 1997, Drugs Aging 10:473-485 and Smith, 2000, J. Urol. 163:248). Mitoxantrone and prednisone are the only FDA approved treatment combinations approved for hormone refractory prostate cancer. Myelosuppression and neutropenia are the major toxicities that are developed.

Other approaches currently under investigation include immunological approaches using prostate specific antigen (PSA) and cytokines such as IL-2, IL-6, IL-7, GM-CSF and TNF and the use of angiogenesis inhibitors. The neovasculature in endothelial cells is a therapeutic target for an antiangiogenic agent.

Acridines

A number of derivatives of acridine have been studied for antitumor activity. Earlier work showed that 1-nitro-9-alkylaminoalkylaminoacridines had good antitumor activity (see, for example, U.S. Pat. No. 4,139,531, Gniazdowsk et al., 1995, Gen. Pharmacol. 26:473, Ledochowski, 1976, Mat. Med. Pol. 8:237, Mazerska et al., 1984, Eur. J. Med. Chem. 19:199, Pawlak et al., 1984, Cancer Res. 44:4829, EP 38572).

Compositions of acridines and other antitumor agents have been formulated. For example, U.S. Pat. No. 5,891,864 discloses anti-cancer compositions comprising acridine derivatives and a guanosine compound. Compounds specifically disclosed include acriflavine neutral, acriflavine, acridine orange, acridine yellow G, diacridine, aniline mustard, guanosine, guanosine hydrate and isoguanosine. It is stated that acridine compounds alone have a small anti-cancer effect and guanosine compounds have none, so the guanosine compounds boost the anti-cancer effect of the acridine derivatives. It is noted that these compositions may be used to treat lung cancer, hepatoma, leukemia, solid tumor and epithelial tissue carcinomas. It is also mentioned that the compositions may also comprise an enhanced anti-tumor effective amount of an immunomodulator, anti-tumor agent or pharmaceutically acceptable carrier.

U.S. Pat. No. 5,759,514 discloses a conjugate for tumor therapy comprising a tumor cell-targeting protein or polypeptide and a radiolabeled nucleic acid-targeting small molecule. This conjugate may bind to the surface of the tumor cell and is subsequently endocytosed. The conjugate once endocytosed, may be lytically decomposed to the radiolabeled small molecule. This radiolabeled small molecule may enter the nucleus of the tumor cell. The small molecule may bind to the tumor cell nucleic acid and the radiolabel may decompose the tumor cell nuclei. The tumor cell targeting protein or polypeptide includes an antibody or fragment thereof, polypeptide hormone or growth factor. The small molecule may be a fluorescein, an acridine such as 3-acetamido-5-iodo-6-aminoacridine or nitracrine, a diacridine, ethidium bromide derivatives, phenanthridines, anthracyclines, and quinazoline derivatives. The radiolabel is an Auger electron-emitting radioisotope such as $^{125}I$, $^{32}P$, $^{188}Rh$, $^{131}I$, $^{77}Br$, $^{225}At$, and $^{213}Bi$. These conjugates are tested in carcinoma cells.

U.S. Pat. No. 5,696,131 discloses the use of acridine carboxamides in combination with other cytotoxic drugs for treating leukemia, melanoma, testicular, brain, ovarian, lung, advanced colon and breast cancer. Additionally, it is disclosed that acridine carboxamides may be used in combination with another cytotoxic drug, such as a DNA reactive reagent (e.g., cisplatin, cyclophosphamide, bleomycin and carboplatin), a DNA synthesis inhibitor (5-fluorouracil, 5-fluorodeoxyuridine and methotrexate) or an agent which disrupts the mitotic apparatus (taxol and vinca alkaloids) to circumvent multidrug resistance. Furthermore, it is proposed that these compounds may be used with a "rescue" treatment with a second drug that by itself is not an active agent but displaces the acridine carboxamide from the DNA.

U.S. Pat. No. 5,604,237 discloses acridine analogs with nitro at the 1-position, a ketone at the 9-position and optionally methoxy at the 7-position. Furthermore, the patent discloses compositions comprising these compounds to improve or increase the efficacy of an antitumor drug such as Vinca alkaloids, anthracyclines, taxol and derivatives thereof, podophyllotoxins, mitoxantrone, actinomycin, colchicine, gramicidin D, amsacrine, increase or restore sensitivity of a tumor to an antitumor drug or reverse or reduce resistance of a tumor to an antitumor drug. No synergism is disclosed.

U.S. Pat. No. 4,603,125 describes antitumor acridine analogs and pharmaceutical compositions containing these analogs. isotonic and absorption delaying agents and the like".

U.S. Pat. No. 3,694,447 discloses complexes of phosphanilic acid and aminoacridines. These complexes may be used as antibacterial and antifungal agents. The aminoacridine may also have a nitro group on the acridine ring.

Ceci et al., 1996, Inorg. Chem. 35:876 describes results of coordination studies of 1-nitro-9-[2-(dialkylamino)ethylamino]acridines with platinum. This compound appears to be very reactive toward platinum. This is due to the severe steric interactions between the 1-nitro and the 9-alkylamino groups in the peri positions of the acridine ring system.

Gniazdowski et al., 1982, Cancer Letters 15:73 shows that five substituted 1-nitro-9-aminoacridine derivatives show an irreversible thiol-dependent inhibitory effect on RNA synthesis in an in vitro system. In the absence of sulhydryl compounds no inhibitory effect is observed.

Szumiel et al., 1980, Neoplasma 6:697 describes the results of combined treatment with X-rays and nitracrine in murine lymphoma cells. It appears that this combined treatment gave additive effects.

OBJECTS OF THE INVENTION

It is clearly advantageous to treat a mammal having a cancerous tumor, particularly a human patient, with a composition containing substances that act on separate targets in the tumors. However, there is always a risk that a composition comprising two or more substances may contain one substance that can modulate the effect of another substance There is clearly a need to develop combination therapeutic approaches that can combine either drugs or different treatment modalities that can at least act in a concerted manner.

Therefore, it is an object of the invention to provide such compositions comprising agents and treatment modalities that act in such a manner. In particular, it is an object of the invention to provide compositions and treatment methods comprising an agent that inhibits tumor growth, particularly, a 1-nitroacridine and another substance that acts at another target area of the tumor cell. In a specific embodiment, this other substance may be a substance that acts to inhibit the nutrient supply route of the tumor cell and thus targets vascularization, e.g., an antiangiogenic agent.

SUMMARY OF THE INVENTION

The invention is directed to compositions comprising a 1-nitroacridine derivative(s) and a tumor inhibiting substance(s). In a specific embodiment, the tumor includes but is not limited to prostrate cancer, breast cancer, colon cancer, lymphoma, sarcoma and leukemia.

In yet another specific embodiment, a 1-nitroacridine derivative(s) and a tumor inhibiting substance(s) or said compositions comprising a 1-nitroacridine derivative(s) and a tumor inhibiting substance(s) may be each administered to a mammal in amounts effective to inhibit or prevent the growth of a tumor and/or inhibit or prevent metastases of said tumor. In one embodiment, the composition comprises at least one 1-nitroacridine derivative and at least one antiangiogneic substance. In another embodiment, the composition comprises at least one 1-nitroacridine derivative selected from the group consisting of a 1-nitro-9-hydroxyalkylaminoacridine and 1-nitro-9-alkoxyalkylaminoacridine derivative and at least one tumor inhibitor substance. In a most specific embodiment, the composition comprises at least one 1-nitroacridine derivative selected from the group consisting of a 1-nitro-9-hydroxyalkylaminoacridine and 1-nitro-9-alkoxyalkylaminoacridine derivative and at least one antiangiogenic substance.

The invention is also directed to a method for inhibiting or preventing the growth of a tumor, particularly, a prostate tumor, and/or inhibiting or preventing metastases of a tumor in a mammal comprising administering to said mammal an amount of a 1-nitroacridine derivative(s) and a tumor inhibiting substance(s) or said compositions comprising a 1-nitroacridine derivative(s) and a tumor inhibiting substance(s) in amounts effective to inhibit or prevent tumor growth and/or inhibit or prevent metastases of said tumor.

The invention is further directed to the use of a 1-nitroacridine derivative(s) and a tumor inhibiting substance(s) for the manufacture of a medicament for inhibiting or preventing tumor growth and/or preventing or inhibiting metastases of said tumor.

DETAILED DESCRIPTION OF THE INVENTION

Figure 1:
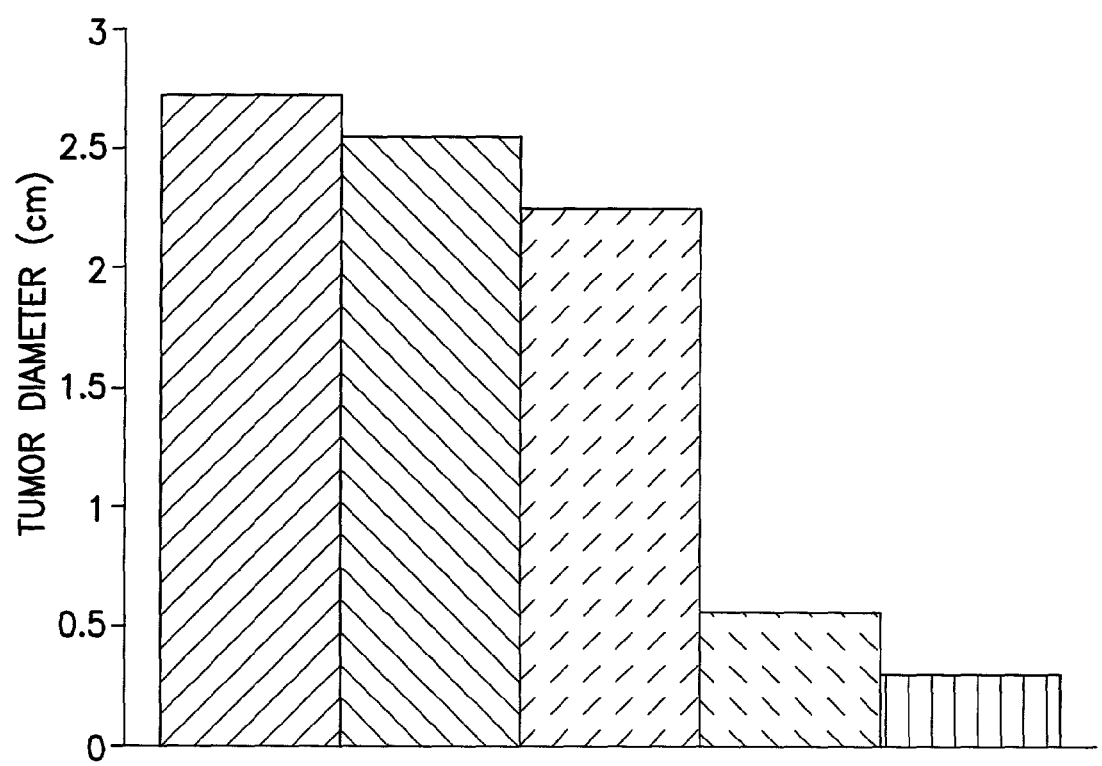
FIG. 1 shows the reduction of MAT-LyLu tumors by 1-nitro-9-hydroxyethylaminoacridine+the antiangiogenic agent, combretastatin. ■Control, ▧mitroxantrone, ▨1-nitro-9-hydroxyethylaminoacridine, ▩mitroxantrone+combretastatin, ■combretastatin+1-nitro-9-hydroxyethylaminoacridine.
Animals are randomized in different groups and are treated with the following drugs: 1-nitro-9-hydroxyethylaminoacridine, 0.6 mg/kg; mitroxantrone, 0.6 mg/kg; combretastatin, 10 mg/kg. Treatment is started when tumors become palpable (0.25 to 0.5 cm diameter) and is continued twice a week for three weeks.

The invention is directed to compositions comprising a 1-nitroacridine derivative(s) and a tumor inhibiting substance(s) as well as methods for using comprising a 1-nitroacridine derivative(s) and a tumor inhibiting substance(s) to inhibit or prevent tumor growth and/or inhibit or prevent metastases.

1-Nitroacridine Derivatives

The 1-nitroacridine derivatives used may be those known in the art (see, for example, U.S. Pat. Nos. 5,604,237, 4,139,531, Gniazdowsk et al., 1995, Gen. Pharmacol. 26:473, Ledochowski, 1976, Mat. Med. Pol. 8:237, Mazerska et al., 1984, Eur. J. Med. Chem. 19:199, Pawlak et al., 1984, Cancer Res. 44:4829). In a specific embodiment, they may be a 1-nitro-9-alkylaminoacridine derivative (see, for example, EP 38572). In a more specific embodiment, the derivative is a 1-nitro-9-hydroxyalkylaminoacridine, 1-nitro-9-alkoxyalkylaminoacridine or 1-nitro-9-alkylcarboxyalkylaminoacridine. In a most specific embodiment, the 1-nitroacridine derivative is selected from the group consisting of 1-nitro-9-hydroxyethylaminoacridine, 9-(2'-hydroxyethylamino)-4-methyl-1-nitroacridine, 9-(2'-hydroxyethylamino)-7-methoxy-1-nitroacridine, 9-(2'-hydroxyethylamino)-7-methoxy-4-methyl-1-nitroacridine, 9-(2'-acetoxyethylamino)-1-nitroacridine, 9-(2'-propionoxyethylamino)-1-nitroacridine, 9-(3'-hydroxypropylamino)-7-methoxy-1-nitroacridine, 9-(3'-hydroxypropylamino)-4-methyl-1-nitroacridine, 9-(2'-acetoxyethylamino)-4-methyl-1-nitroacridine, 9-(2'-propionoxyethylamino)-4-methyl-1-nitroacridine, 9-(3'-acetoxypropylamino)-4-methyl-1-nitroacridine, 9-(2'-propionoxypropylamino)-4-methyl-1-nitroacridine, 9-(2'-hydroxyethylamino)-4-methoxy-1-nitroacridine, 9-(3'-hydroxypropylamino)-4-methoxy-1-nitroacridine, 9-(4'-hydroxybutylamino)-4-methoxy-1-nitroacridine, 9-(4'-hydroxybutylamino)-7-methoxy-1-nitroacridine and 9-(2'-acetoxyethylamino)-7-methoxy-4-methyl-1-nitroacridine.

In another specific embodiment, the derivative may be a novel acridine compound having the structure I

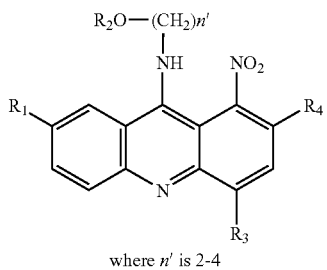

where $n'$ is 2-4 wherein when $R_1$ is H, $R_2$ is H or $CO(CH_2)_nCH_3$, where n=1-8, $R_3$ is H, $(CH_2)_nCH_3$, where n=0-1 or $O(CH_2)_nCH_3$, where n=0-1 and $R_4$ is H, $(CH_2)_nCH_3$, or $O(CH_2)_nCH_3$, where n=0-1;

wherein when $R_1$ is $O(CH_2)_nCH_3$, where n=0-1, and $R_2$ is H, $R_3$ and $R_4$ is H and wherein when $R_1$ is $O(CH_2)_nCH_3$, where n=0-1 and $R_2$ is $CO(CH_2)_nCH_3$, where n=1-8 $R_3$ is H, $(CH_2)_nCH_3$, where n=0-1 or $O(CH_2)_nCH_3$, where n=0-1, $R_4$ is H, $(CH_2)_nCH_3$, or $O(CH_2)_nCH_3$, where n=0-1 or salts thereof.

The compounds of this invention are prepared by series of reactions as shown on Scheme 1

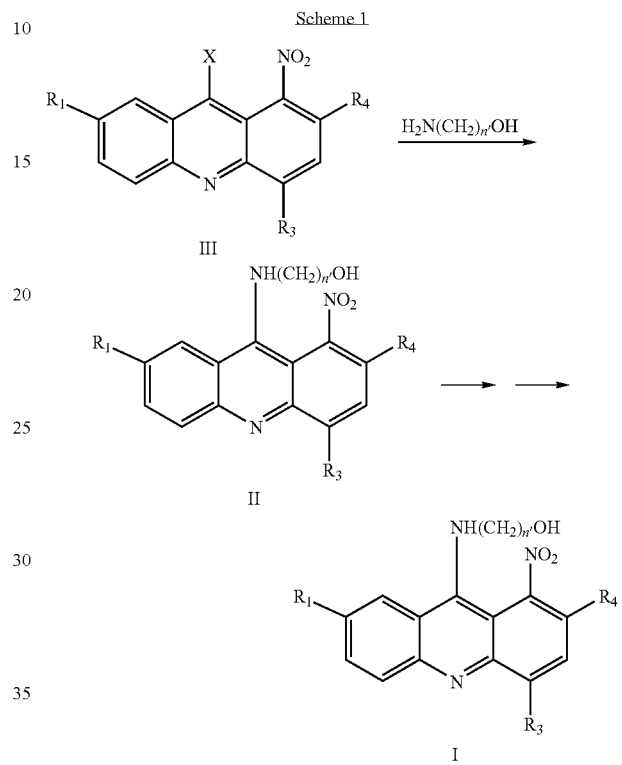

where $R_1$-$R_4$ are as hereinbefore defined and X is Cl, phenoxy or pyridinium salt.

The compound III which may be employed as starting material in the practice of the present invention may be prepared in accordance with the teaching set forth in Ledochowski, A. Mat. Med. Pol. 1976, 3: 237 for 9-amino-1-nitroacridine derivatives ($R_1$=$R_3$=H); in Yekundi, K. G. et al Chem. Ber. 1957, 90:2448 for 9-amino-7-methoxy-1-nitroacridines ($R_1$=$OCH_3$, $R_3$=H); and in Horowska, B.; Ledóchowski, A. Rocz. Chem. 1968, 42:1351 for 9-amino-4-methyl or 4-methoxy-1-nitroacridines ($R_1$=H, $R_3$=$OCH_3$ or $CH_3$). A method for obtaining III (9-amino-7-methoxy-4-methyl-1-nitroacridines) is presented on the Scheme 2.

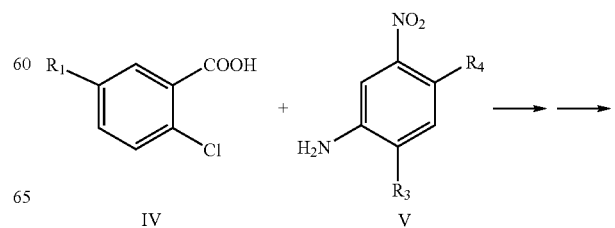

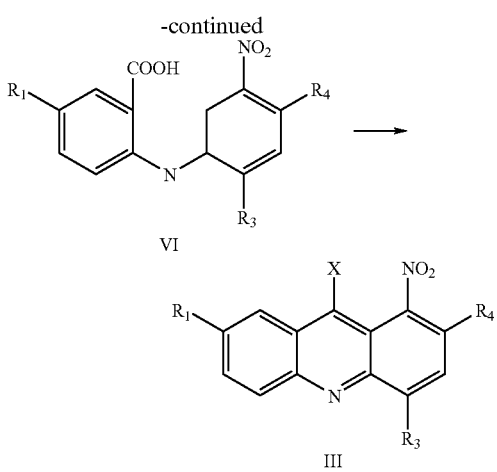

The substituted 1-nitroacridines of this invention of general formula III may be prepared by condensation of an appropriate substituted o-halogenobenzoic acid and aniline derivative or alternatively, of substituted anthranilic acid and halogenobenzene derivative, the condensation being affected by heating at least equimolar amounts of the reactants in the presence of an acid acceptor and catalytic amounts of copper or/and its salts. Preferably, the benzoic acid derivatives may be used as their salts with alkali metals, such as sodium or potassium salts. The heating of the reactants takes place without a solvent or in a suitable solvent at temperatures from 80 to 180° C. Suitable solvents include but are not limited to such organic solvents as dimethylformamide, dimethylacetamide, diphenyl ether, nitrobenzene, higher aliphatic alcohols, such as amyl alcohol. Suitable acid acceptors include tertiary amines and alkali metals salts, such as sodium and potassium carbonates and the like. If desired, the reaction solvent itself may serve as the acid acceptor, such as when the dimethylaniline is employed as the solvent. The desired condensation product of general formula VI is preferably separated as a solution of its salt in water, and precipitated by an addition of mineral acid, such as hydrochloric acid. The desired product is then removed from the aqueous mixture by filtration, and optionally, purified by usual techniques, such as crystallization from a suitable organic solvent. The condensation products of general formula VI may be cyclized to the acridine derivative by usual methods known in the art (Acheson, R. M. Ed., *Acridines*, Interscience Publishers, NY, London, 1973). In a preferred embodiment of the cyclization, N-phenylanthranilic acid derivative is heated in a solution of phosphorous oxychloride at temperature from 60° C. to reflux, an excess of the reactant is removed by evaporation, and the product isolated by precipitation or extraction using a suitable solvent. Suitable solvents include such organic solvents as chloroform, methylene chloride, benzene, toluene or ether. The formed 9-chloroacridine derivative III is further isolated and purified by the usual techniques. When $R_3$ is H, two isomers are formed. The isomers may be separated by heating III where X=Cl to give pyridinium salts of III which can easily be separated. Those isomers are heated with phenol and give III, where X=OPh.

A method of this invention for obtaining 1-nitro-9-(hydroxyalkylamino)acridine derivatives or their salts of the formula II, wherein substituents $R_1$ and $R_3$ are as hereinbefore defined, comprises reacting a suitable 9-chloro-derivative of formula III or related 9-phenoxy-derivative or related acridinyl-9 pyridinium salt with an appropriate derivative of hydroxyalkylamine in phenol at temperatures from 40 to 120° C. The desired product is than isolated by precipitation of its salt with non-polar organic solvent. Suitable organic solvents include ethyl ether, benzene, toluene, tetrahydrofurane. Alternatively, the desired product may be isolated by alkalization of the reaction mixture and extraction of the product with a suitable, water immiscible solvent. The suitable, water immiscible solvents include ethyl ether, benzene, toluene, chloroform, ethyl acetate and the like.

Alternatively, condensation of suitable 9-chloro-derivative of formula III or related 9-phenoxy-derivative or related acridinyl-9 pyridinium salt with an appropriate derivative of hydroxyalkylamine may be performed in a suitable polar solvent in a presence of acidic catalyst. Suitable polar solvents include alcohols, polar aprotic solvents or hydroxyalkylamine itself. Suitable acidic catalyst include mineral acids, strong organic acids or phenol.

A method of this invention for obtaining 1-nitro-9-(alkoxyalkylamino)acridine derivatives or their salts of the formula I, wherein substituents $R_1$-$R_5$ are as hereinbefore defined, comprises reacting of suitable 1-nitro-9-(hydroxyalkylamino)acridine derivative with a suitable acylating agent. A suitable acylating agent includes but is not limited to carboxylic acids, related acid chlorides, acid anhydrides or others known in the art. In a preferred embodiment of the reaction in the present invention, acylating agent is formed from carboxylic acid in situ in the reaction mixture. The reaction is preferably conducted in suitable solvents. Suitable solvents include organic solvents such as haloalkanes, e.g., chloroform, aromatic hydrocarbons, e.g. benzene and toluene, aliphatic ethers or aliphatic cyclic ethers, or carboxylic acids, preferably the same acid which serves as the acylating agent. The condensation is typically done at low temperature, preferably from −30° C. to room temperature, and products are isolated by usual methods.

Tumor Inhibitor Substances

A "tumor inhibitor substance" is a chemical substance other than a 1-nitroacridine described above that inhibits the growth of a tumor. Such a substance may be an antiangiogenic substance. In a specific embodiment, the antiangiogenic substance may be, e.g., interferon-gamma, endostatin, combretastatin (see, for example, Petit et al., 1995, Anti-Cancer Drug Design 10:299-309, Dang et al., 1997, Cancer Res. 57:1829-1834, U.S. Pat. Nos. 5,561,122 and 4,996,237), phenstatin (WO/9934788, Pettit et al., 1998, J. Med. Chem. 41:1688-1695), pancratistatin (Pettit et al., 1995, J. Nat. Prod. 58:57-43 and U.S. Pat. Nos. 5,529,989 and 4,985,436), fumagillin (Figg et al., 2000, Expert Opin. Investig. Drugs 9:1383-1396) or TNP-470.

The tumor inhibitor substance may be any agent that inhibits tumor vasculature or biochemical processes that affect new blood vessel growth.

Alternatively, the tumor inhibitor substance may be a cytokine such as the members of the interleukin family (IL-1, IL-2, IL-6, IL-7, IL-12, IL-15) GM-CSF and tumor necrosis factor, tumor growth factor alpha or beta, interferons alpha/beta or gamma. In another embodiment, the tumor inhibitor substance may be a nucleic acid synthesis inhibitor(s), cell cycle inhibitor(s), antimitotic agent(s) or growth factor inhibitors. Specific examples include but are not limited to vinca alkaloids, cyclophosphamide, doxorubicin, mitoxantrone, suramin or estramustine.

The tumor inhibitor substance may also include but is not limited to random synthetic peptides generated from combinatorial libraries and may modulate tumor vasculature, induce cytokines, act as antimitotic agents, modulate cell growth, cytotoxic agents, cytostatic agents, and/or induce apoptosis. Other tumor inhibitor substances may be steroids or hormone inhibitors.

Compositions

In one embodiment, the mammal and specifically, the human patient, is administered a composition comprising a 1-nitroacridine derivative, then subsequently administered a composition comprising a tumor inhibitor substance. In another embodiment, the mammal is administered a composition comprising a tumor inhibitor substance and a 1-nitroacridine derivative. In yet another embodiment, the mammal is administered the two compositions simultaneously. A composition comprising a tumor inhibitor substance(s) may comprise a combination of a substance that inhibits the growth of solid tumors by targeting the epithelial cells and a substance that targets the tumor vasculature endothelial cells. The specific cancers which can be treated with the composition of the present invention can include prostate, colon cancer, lymphoma, breast cancer, leukemia, sarcoma and/or lymphoma.

In yet a further embodiment, the composition of the present invention may comprise both the 1-nitroacridine and the tumor inhibitor substance(s). The combined composition of the 1-nitroacridine derivative and the tumor inhibitor substance according to the present invention can be formulated by means of conventional methods for preparing pharmaceutical preparations. The 1-nitroacridine derivative(s) and the tumor inhibitor substance(s) are mixed in a suitable ratio, for example, about 1:15 to about 1:2 in a light resistant container.

The composition may further comprise pharmaceutically acceptable carriers or excipients, formulated into the pharmaceutical formulation suitable for topical, parenteral or oral administration which can be topically, parenterally or orally administered to inhibit or prevent the growth of a tumor in a mammal and particularly a human. Parenteral administration includes intravenous, intraarterial, subcutaneous, intraperitoneal or intramuscular injection or infusion; or intracranial, e.g., intrathecal or intraventricular, administration.

A pharmaceutically acceptable carrier or excipient is a pharmaceutically acceptable solvent, suspending agent or any other pharmacologically inert vehicle for delivering one or more of the compounds of the present invention to an animal. The excipient may be liquid or solid and is selected, with the planned manner of administration in mind, so as to provide for the desired bulk, consistency, when combined with the compound of the present invention and the other components of a given pharmaceutical composition. Typical pharmaceutical carriers include, but are not limited to, binding agents (e.g., pregelatinized maize starch, polyvinylpyrrolidone or hydroxypropyl methylcellulose); fillers (e.g., lactose and other sugars, microcrystalline cellulose, pectin, gelatin, calcium sulfate, ethylcellulose, polyacrylates or calcium hydrogen phosphate); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate); disintegrants (e.g., starch, sodium starch glycolate); and wetting agents (e.g., sodium lauryl sulphate).

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug that may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Although the effective amount of the composition according to the present invention can be varied depending upon various factors including the subject to be administered, severity of cancer to be treated, etc., generally in an adult man (based on a body weight of 60 kg), the dosage may be in the range of about 0.5 to about 2 mg/kg of body weight for the 1-nitroacridine derivative and 0.5 to about 20 mg/kg of body weight for the tumor inhibitor substance per day for oral administration about 0.2 to about 1 mg/kg of body weight 0.2 to about 10 mg/kg of body weight per day weight for the tumor inhibitor substance for intravenous administration and in the range of about 0.1 to about 0.5 mg/kg of body weight for the 1-nitroacridine derivative and 0.1 to about 5 mg/kg of body weight for the tumor inhibitor substance per day, for intramuscular injections.

The composition of the present invention can include other medicinal components having immunoadjuvant activity or anti-cancer activity, or can be administered in combination with another immunoadjuvant or anti-cancer agent. As the immunoadjuvant which can be included in, or combined with, the composition according to the present invention, the followings can be mentioned: monoclonal antibodies, immunoagitators, human immunoglobulins or cytokines such as interferons or interleukins or sugar specific proteins such as lectins, As the anti-cancer agent which can be used for this purpose, the followings can be mentioned: synthetic anti-cancer agents, for example, alkylating agents such as chlorambucil, melphalan, cyclophosphamide, nitrosourea amine compounds such as mannomustine, ethylenediamines such as uredepa; anti-metabolic agents, for example, folic acid antagonists such as methotrexate or aminoptherine, purine antagonists such as mercaptopurine, pyrimidine antagonists such as proxuridine, or 6-azauridine, sugar-based antagonists such as mitobronitol, or cisplatin, picivanil, 5-fluorouracil(5-FU); anti-cancer antibiotics, for example, actinomycin, THP-adriamycin, mitomycin, etc.; hormone antagonists such as tamoxifen; and alkaloid plant components such as demecolcine. Additionally, the composition of the present invention may comprise more than one 1-nitroacridine derivative.

EXAMPLES

Synthesis of 1-Nitroacridines

1-Nitro-9-Hydroxyethylaminoacridine

This compound is synthesized generally using the methods described in EP 38579. Specifically, 2 g of 2-amino-ethanol hydrochloride is added to 6.4 g of 1-nitro-9-phenoxyacridine dissolved in 20 g of freshly distilled phenol. The mixture is heated for 40 minutes at a temperature of 80° C. and then cooled, diluted with ether. It is then poured into dry ether that was acidified with an ethereal solution of hydrogen chloride. The orange colored precipitate of 1-nitro-9-(2-hydroxyethylamino)-acridine hydrochloride, obtained in this way is filtered and crystallized from dry ethanol. The melting point of the compounds obtained was 170° C., with decomposition. Yield 91%. Elementary analysis for the formula: $C_{15}H_{14}N_3O_3Cl$:calculated:56.47%; C, 4.42%; H, 13.17%; N. determined: 56.44%; C, 4.40%; H, 13.03%; N.

9-(2'-hydroxyethylamino)-4-methyl-1-nitroacridine

4-Methyl-1-nitro-9-phenoxyacridine (0.33 g) is dissolved in phenol (10 g), ethanolamine hydrochloride (0.2 g) is added and the mixture is heated at 80° C. for 0.5 hour. The reaction mixture is cooled to room temperature, diluted with ether, slowly poured into dry ether (200 ml) and acidified with ethereal solution of hydrogen chloride. The resulting precipitate is filtered off, washed with ether and crystallized from absolute ethanol to give 9-(2'-hydroxyethylamino)-4-methyl-1-nitroacridine monohydrochloride as orange crystals (0.27 g, 84%), m.p. 238° C. (decomp.) $^1$H NMR ($d_6$DMSO): δ 2.45 (s, 3H, $CH_3$), 3.48(q, 2H, H-2'), 3.65 (t, 2H, H-1'), 4.3 (t, 1H, OH), 7.1 (t, 1H, H-7), 7.24 (d, 1H, J =7.8 Hz, H-2), 7.35 (d, 1H, J=7.8 Hz, H-3), 7.5 (t, 1H, H-6), 7.65 (d, 1H, J=8 Hz, H-5), 7.75 (d, 1H, J=8.0 Hz, H-8).

9-(2'-hydroxyethylamino)-7-methoxy-4-methyl-1-nitroacridine

7-Methoxy-4-methyl-1-nitro-9-phenoxyacridine (0.72 g) is dissolved in phenol (20 g). Ethanolamine hydrochloride (0.2 g) is added and the mixture is heated at 80° C. for 1.5 hour. The reaction mixture is cooled to room temperature, diluted with dry ether, slowly poured into dry ether (300 ml) and acidified with ethereal solution of hydrogen chloride. The resulting precipitate is filtered off, washed twice with ether and crystallized from absolute methanol to give 9-(2'-hydroxyethylamino)-7-methoxy-4-methyl-1-nitroacridine monohydrochloride as orange crystals (0.6 g, 86%), m.p. 200° C. (decomp.) $^1$H NMR ($d_6$DMSO): δ 2.60 (s, 3H, $CH_3$), 3.50 (s, 4H, H-1', H-2'), 4.00 (s, 3H, $OCH_3$), 7.66 (dd, 1H, $J_1$=9.3 Hz, $J_2$=2.5 Hz, H-6), 7.85 (d, 1H, J=8.2 Hz, H-3), 8.02 (s, 1H, H-8), 8.15 (d, 1H, J=7.8 Hz, H-2), 8.22 (d, 1H, J=7.8 Hz, H-5).

9-(2'-hydroxyethylamino)-7-methoxy-1-nitroacridine

7-Methoxy-1-nitro-9-phenoxyacridine (0.69 g) is dissolved in phenol (20 g). Ethanolamine hydrochloride (0.2 g)

is added and the mixture is heated at 100° C. for 1.5 hour. The reaction mixture is cooled to room temperature, diluted with dry ether (100 ml), slowly poured into dry ether (300 ml) and acidified with ethereal solution of hydrogen chloride. The resulting precipitate is filtered off, washed twice with ether and crystallized from absolute methanol-ether to give 9-(2'-hydroxyethylamino)-7-methoxy-1-nitroacridine monohydrochloride (0.58 g, 83% yield), m.p. 220° C. (decomp.) $^1$H NMR (d$_6$DMSO): δ 3.45 (t, 2H, H-2'), 3.65 (t, 2H, H-1'), 3.80 (s, 3H, OCH$_3$), 7.30 (dd, 1H, J$_1$=9.3 Hz, J$_2$=2.5 Hz, H-6), 7.35 (d, 1H, J=2.5 Hz, H-8), 7.40 (d, 1H, J=9.3 Hz, H-5), 7.7 (m, 2H, H-3, H-4), 7.87 (m, 1H, H-2).

9-(2'-Acetoxyethylamino)-1-nitroacridine

Thionyl chloride (7.5 ml) is added to a stirred, cooled to −20° C. acetic acid (30 ml). Next, at the same temperature, 9-(2'-hydroxyethylamino)-1-nitroacridine (0.5 g) is added in portions, and the mixture is stirred at room temperature for 24 hours. The solvent is distilled off under reduced pressure, the residue washed several times with 10% aqueous sodium bicarbonate and water, dried under vacuum, and crystallized from absolute ethanol ethereal hydrogen chloride solution to give 9-(2'-acetoxyethylamino)-1-nitroacridine (0.4 g, 80% yield), m.p. 170-2° C. (decomp.). $^1$H NMR (d$_6$DMSO): δ 1.6 (s, 3H, CH$_3$), 3.85 (t, 2H, H-1'), 4.2 (t, 2H, H-2'), 7.10 (t, 1H, H-7), 7.25 (d, 1H, J=7.5 Hz, H-2) 7.35 (d, 1H, J=7.8 Hz, H-5), 7.42 (d, 1H, J=8.3 Hz, H-4), 7.50 (d, 1H, J=7.5 Hz, H-3), 7.60 (d, 1H, J=7.8 Hz, H-6), 7.82 (d, 1H, J=7.8 Hz, H-8).

9-(3'-Hydroxypropylamino)-7-methoxy-1-nitroacridine

7-Methoxy-1-nitro-9-phenoxyacridine (0.69 g) is dissolved in phenol (20 g), 3-aminopropanol hydrochloride is added and the mixture is heated at 100° C. for 1.5 hour. The reaction mixture is cooled to room temperature, diluted with dry ether (100 ml), and slowly poured into dry ether (300 ml) preacidified with ethereal solution of hydrogen chloride. The resulting precipitate is filtered off, washed twice with ether and crystallized from absolute methanol-ether (3:1) to give 9-(3'-hydroxypropylamino)-7-methoxy-1-nitroacridine monohydrochloride as orange crystals (0.5 g, 72% yield), m.p. 208-210° C. (decomp.) $^1$H NMR (d$_6$DMSO): δ 1.75 (t, 2H, H-2'), 3.45 (q, 2H, H-3'), 3.74 (t, 2H, H-1'), 4.32 (t, 1H, OH), 7.15 (dd, 1H, J$_1$=2.7 Hz, J$_2$=9.0 Hz, H-6), 7.20 (d, 1H, J=9.5 Hz, H-2), 7.25 (d, 1H, J=9.3 Hz, H-5), 7.3 (d, 1H, J=7.7 Hz, H-8), 7.45 (t, 1H, H-3).

9-(2'-Propionoxyethylamino)-1-nitroacridine

Thionyl chloride (8 ml) is added to a stirred, cooled to −20° C. propionic acid (60 ml). Next, at the same temperature, 9-(2'-hydroxyethylamino)-1-nitroacridine (0.5 g) is added in portions, and the mixture is stirred at room temperature for 24 hours. The solvent is distilled off under reduced pressure, the residue washed several times with 10% aqueous sodium bicarbonate and water, dried under vacuum, and crystallized from absolute ethanol-ethereal hydrogen chloride solution to give 9-(2'-propionoxyethylamino)-1-nitroacridine hydrochloride as yellow crystals (0.37 g, 65% yield), m.p. 98-100° C. $^1$H NMR (NMR of the free base) (d$_6$DMSO): δ 1.00 (t, 3H, H-3''), 2.30 (q, 2H, H-2''), 3.90 (t, 2H, H-1'), 4.20 (t, 2H, H-2'), 7.10 (t, 1H, H-7), 7.25 (d, J=8.8 Hz, H-2), 7.30 (d, 1H, J=8.3 Hz, H-5), 7.36 (d, 1H, J=9.3 Hz, H-4), 7.38, (t, 1H, H-3), 7.51 (t, 1H, H-6), 7.82 (d, 1H, J=7.3 Hz, H-8), 10.84 (s, 1H, NH).

9-(2'-Hydroxyethylamino)-4-methoxy-1-nitroacridine

4-Methoxy-1-nitro-9-phenoxyacridine (0.346 g) is dissolved in phenol (30 g), ethanolamine hydrochloride (0.12 g) is added and the mixture is heated at 80° C. for 1.5 hour. The reaction mixture is cooled to room temperature, diluted with dry ether (20 ml), slowly poured into dry ether (200 ml) and acidified with ethereal solution of hydrogen chloride. The resulting precipitate is filtered off, washed several times with ether and crystallized from absolute ethanol-ether (5:1) to give 9-(2'-hydroxyethylamino)-4-methoxy-1-nitroacridine monohydrochloride as yellow crystals (0.27 g, 77% yield), m.p. 210-212° C. (decomp.) $^1$H NMR (for a free base) (d$_6$DMSO): δ 10.18 (s, 1H, NH), 7.78 (d, 1H, J=7.8 Hz, H-8), 7.67 (d, 1H, J=8.3 Hz, H-5), 7.47 (t, 1H, J=7.8 Hz, H-6), 7.36 (d, 1H, J=8.8 Hz), 7.10 (m, 2H, H-3, H-7), 4.31 (t, 1H, J=5.4 Hz, OH), 3.70 (t, 2H, J=6.4 Hz, H-1'), 3.64 (q, 2H, J=6.3 Hz, H-2').

9-Chloro-7-methoxy-4-methyl-1-nitroacridine

N-(2'-methyl-5'-nitrophenyl)-5-methoxyanthranilic acid (7.2 g) is heated in phosphorous oxychloride (60 ml) at 120° C. for 1 hour. Excess phosphorous oxychloride is distilled off under reduced pressure, and the residue is poured slowly into a stirred mixture of chloroform, concentrated ammonium hydroxide and ice. The separated chloroformic layer is washed with water and dried using magnesium sulfate. Chloroform is evaporated to dryness, and the residue is crystallized from benzene to give 9-chloro-7-methoxy-4-methyl-1-nitroacridine (6.1 g, 68% yield), m.p. 227-228° C. $^1$H NMR (d$_6$DMSO): δ 8.23 (d, 1H, J=9.3 Hz), 8.13 (d, 1H, J=7.3 Hz), 7.79 (bd, 1H, J=8.3 Hz), 7.71 (dd, 1H, J$_1$=9.3 Hz, J$_2$=2.9 Hz), 7.58 (d, 1H, J=2.9 Hz), 4.02 (s, 3H), 2.85 (s, 3H).

N-(2'-methyl-5'-nitrophenyl)-5-methoxyanthranilic acid

Potassium salt of 2-bromo-5-methoxybenzoic acid (23 g) and 2-methyl-5-nitroaniline (40 g) are stirred and heated at 110° C. in the presence of 50 mg of catalytic copper for 50 minutes. Next, the reaction mixture is poured on 5% solution of potassium hydroxide in water (600 ml) and cooled. The formed precipitate is filtered off, washed with water, and the collected solutions are acidified with hydrochloric acid to pH 5. The formed solid is filtered off and crystallized from methanol—acetone (2:1) to give N-(2'-methyl-5'-nitrophenyl)-5-methoxyanthranilic acid (11.2 g, 56% yield), m.p. 219-221° C. $^1$H NMR (d$_6$DMSO): δ 9.20 (bs, 1H), 7.88 (d, 1H, J=1.9 Hz), 7.65 (dd, 1H, J$_1$=7.8 Hz, J$_2$=1.9 Hz), 7.44 (d, 1H, J=8.3 Hz), 7.43 (d, 1H, J=2.9 Hz), 7.26 (d, 1H, J=8.8 Hz), 7.19 (dd, 1H, J$_1$=8.8 Hz, J$_2$=2.9 Hz), 3.68 (s, 3H), 2.27 (s, 3H).

9-(3'-hydroxypropylamino)-4-methyl-1-nitroacridine

4-Methyl-1-nitro-9-phenoxyacridine (0.66 g) is dissolved in phenol (15 g), 3-aminopropanol hydrochloride is added and the mixture is heated at 80° C. for 1.5 hour. The reaction mixture is cooled to room temperature, diluted with dry ether (50 ml) and acidified with ethanol solution of hydrogen chloride. The resulting precipitate is filtered off, washed several times with ether and crystallized from absolute ethanol to give 9-(3'-hydroxypropylamino)-4-methyl-1-nitroacridine hydrochloride as yellow crystals (0.54 g, 76% yield), m.p. 205-206° C., anal. C$_{17}$H$_{18}$N$_3$O$_3$Cl (C,H,N). $^1$H NMR (D$_2$O):

δ 1.65(m, 2H, H 2'), 2.40(s, 3H, CH$_3$), 3.20(q, 2H, H-3'), 3.40(m, 2H, H-1'), 7.22(t, 1H, H-7), 7.48(d, 1H, J=7.8 Hz, H-3), 7.48(d, 1H, J=7.8 Hz, H-3), 7.54(d, 1H, J=8.3 Hz, H-6), 7.60(t, 1H, H-5), 7.74(t, 1H, H-8).

9-(2'-acetoxyethylamino)-4-methyl-1-nitroacridine

Thionyl chloride (8 ml) is added to a stirred, cooled to −20° C. acetic acid (30 ml). At the same temperature 9-(2-hydroxyethylamino)-4-methyl-1-nitroacridine hydrochloride (0.6 g) is added in portions. The reaction mixture is stirred at room temperature for 20 hours. Next, the solvent is distilled off under reduced pressure, the residue washed several times with 10% aqueous sodium bicarbonate and water, dried under vacuum and crystallized from dry methanol-ether solution to give 9-(2'-acetoxyethylamino)-4-methyl-1-nitroacridine (72% yield), m.p. 210-212° C., anal. C$_{18}$H$_{18}$N$_3$O$_4$Cl (C,H,N). $^1$H NMR (D$_2$O): δ2.45 (s, 3H, CH$_3$'), 2.6(s, 3H CH$_3$), 3.25(t, 2H, H-1'), 3.65(t, 2H, H-2'), 7.35(t, 1H, H-7), 7.58(d, 1H, J=8.8 Hz, H-2), 7.66(d, 1H, J=8.3 Hz, H-3), 7.7(t, 1H, H-6), 7.84(d, 1H, J=7.8 Hz, H-5), 7.9(d, 1H, J=8.1 Hz, H-8).

9-(2'-propionoxyethylamino)-4-methyl-1-nitroacridine

Thionyl chloride (10 ml) is added to a stirred, cooled to −20° C. propionic acid (50 ml) and at the same temperature 9-(2-hydroxyethylamino)-4-methyl-1-nitroacridine (0.55 g) is added in portions, and the mixture is stirred at room temperature for 20 hours. The reaction mixture is distilled off under reduced pressure, washed several times with 10% aqueous sodium bicarbonate and water, dried under vacuum, and crystallized from absolute methanol-ethanol hydrogen chloride solution to give 9-(2-propionoxyethylamino)-4-methyl-1-nitroacridine hydrochloride with 68% yield, m.p. 228-230° C., anal. C$_{19}$H$_{19}$N$_3$O$_4$Cl(C,H,N). $^1$H NMR (d$_6$DMSO): δ 1.20(t, 3H, H-3"), 2.0(q, 2H, H-2"), 2.8(s, 3H, CH$_3$), 3.9(t, 2H, H-1), 4.0(t, 2H, H-2'), 7.4(t, 1H, H-7), 7.5(d, 1H, J=7.8 Hz, H-3), 7.6(d, 1H, J=8.3 Hz, H-6), 8.0(t, 1H, H-5), 8.4(m, 1H, H-8).

9-(2'-acetoxypropylamino)-4-methyl-1-nitroacridine

Thionyl chloride (20 ml) is added to a cooled to −20° C. and stirred acetic acid (35 ml) and at the same temperature 9-(3'-hydroxypropylamino)-4-methyl-1-nitroacridine (0.5 g) is added in portions. The reaction mixture is stirred at room temperature for 24 hours. The solvent is distilled off under reduced pressure, the residue washed several times with 10% aqueous sodium bicarbonate and water, dried under vacuum and crystallized from absolute ethanol to give 9-(2'-acetoxypropylamino)-4-methyl-1-nitroacridine with 67% yield, m.p. 150-152° C., anal. C$_{19}$H$_{19}$N$_3$O$_4$ (C,H,N). $^1$H NMR (d$_6$DMSO): δ 1.20(t, 3H, H-3"), 1.75(t, 2H, H-2'), 2.4(s, 3H, CH3), 4.0(t, 2H, H-1'), 7.1(t, 1H, H-7), 7.2(d, 1H, J=7.8 Hz, H-2), 7.4(d, 1H, J=7.8 Hz, H-3), 748(t, 1H, H-6), 7.65(d, 1H, J=8.3 Hz, H-5), 7.7(d, 1H, J=8.3 Hz, H-8).

9-(3'-propionoxypropylamino)-4-methyl-1-nitroacridine

Thionyl chloride (25 ml) is added to a cooled to −20° C. and stirred propionic acid (40 ml) and at the same temperature 9-(3-hydroxypropylamino)-4-methyl-1-nitroacridine hydrochloride (0.6 g) is added in portions. The reaction mixture is stirred at room temperature for 20 hours. The solvent is distilled off under reduced pressure, the residue (oil) washed several times with 10% aqueous sodium bicarbonate and water, dried under vacuum and crystallized from dry methanol acidified with ethanol solution of hydrogen chloride give 9-(3'-propionoxypropylamino)-4-methyl-1-nitroacridine hydrochloride (78% yield), m.p. 161-163° C., anal. C$_{20}$H$_{22}$N$_3$O$_1$Cl (C,H,N). $^1$H NMR (d$_6$DMSO): δ 1.0(t, 3H, H-3"), 2.35(q, 2H, H-2"), 2.5(s, 3H, CH$_3$), 4.30(t, 2H, H-1'), 7.15(t, 1H, H-7), 7.26(d, 1H, J=7.8 Hz, H-2), 7.38(d, 1H, J=7.8 Hz, H-3), 7.5(t, 1H, H-6), 7.62(d, 1H, J=8.0 Hz, H-5), 7.8(d, 1H, J=8.2 Hz, H-8).

9-(3'-hydroxypropylamino)-4-methoxy-1-nitroacridine

9-Chloro-4-methoxy-1-nitro-9-acridine (0.4 g) is dissolved in phenol (20 g), 3-aminopropanol (1.5 g) is added and the mixture is heated at 80° C. for 1 hour. The reaction mixture is cooled, diluted with dry ether and acidified with ethanol solution of hydrogen chloride. The resulting precipitate is filtered off, washed with dry ether and crystallized from absolute methanol to give 9-(3-hydroxypropylamino)-4-methyl-1-nitroacridine hydrochloride crystals (74% yield), m.p. 180-183° C., anal. C$_{17}$H$_{18}$N$_3$O$_4$Cl (C,H,N). $^1$H NMR (D$_2$O): δ1.68(s, 2H, H-2'), 3.40(t, 2H, H-3'), 3.50(q, 2H, H-1'), 4.0(s, 3H, OCH$_3$), 7.0(d, 1H, J=8.8 Hz, H-3), 7.27(t, 1H, H-7), 7.49(d, 1H, J=8.3 Hz, H-5), 7.65(t, 1H, H-6), 7.77(d, 1H, J=8.3 Hz, H-8), 7.90(d, 1H, J=8.3 Hz, H-2).

9-(4'-hydroxybutylamino)-4-methoxy-1-nitroacridine

4-Methoxy-1-nitro-9-phenoxyacridine (0.34 g) is dissolved in 20 g of phenol, 4-hydroxyaminobutanol hydrochloride (0.15 g) is added and the mixture is heated at 110° C. for 1.5 hour. The reaction mixture is cooled to room temperature, diluted with dry ether, acidified with ethanol solution of hydrogen chloride. The precipitate is filtered, washed with dry ether and crystallized from absolute ethanol to give 9-(4'-hydroxybutylamino)-4-methoxy-1-nitroacridine hydrochloride (69% yield), m.p. 149-152° C., anal. C$_{18}$H$_{20}$N$_3$O$_4$Cl (C,H,N). $^1$H NMR (D$_2$O ): δ 1.25(t, 2H, H-2'), 3.3(q, 2H, H-4'), 3.4(t, 2H, H-1'), 4.0(s, 3H, OCH$_3$), 7.1(d, 1H, J=8.8 Hz, H-3), 7.5(d, 1H, J=8.8 Hz, H-5), 7.6(t, 1H, H-6), 7.7(d, 1H, J=7.3 Hz, H-8), 7.9(m, 1H, H-2).

9-(4'-hydroxybutylamino)-4-methox-1-nitroacridine hydrochloride

9-Chloro-7-Methoxy-1-nitro-9-acridine (0.37 g), lOg phenol and 4-hydroxyaminobutanol (0.15 g) are heated at 120° C. for 1.5 hour. The reaction mixture is cooled to room temperature, diluted with dry ether and acidified with ethanol solution of hydrogen chloride. The resulting precipitate is filtered, washed with ether and crystallized from methanol-ether (3:1) acidified with ethanol solution of hydrogen chloride to give 9-(4'-hydroxybutylamino)-7-methoxy-1-nitroacridine hydrochloride with 81% yield, m.p. 153-155° C, anal. C$_{18}$H$_{20}$N$_3$O$_4$Cl (C,H,N). $^1$H NMR (D$_2$O): δ 1.68(t, 2H, H-3'), 3.39(t, 2H, H-1'), 3.50(q, 2H, H-2'), 4.0(s, 3H, OCH3), 7.04 (d, 1H, J=8.8 Hz, H-3), 7.27(t, 1H, H-7), 7.49(d, 1H, J=8.3 Hz, H-5), 7.65(t, 1H, H-6), 7.80(d, 1H, J=8.3 Hz, H-8), 7.90 (d, 1H, J=8.8 Hz, H-2).

9-(2'-acetoxyethylamino)-7-methoxy-4-methyl-1-nitroacridine

Thionyl chloride (5 ml) is added to a stirred, cooled to −20° C. acetic acid (20 ml) and at the same temperature 9-(2'- hydroxyethylamino)-7-methoxy-4-methyl-1-nitroacridine hydrochloride (0.3 g) is added in portions, and the mixture is stirred at room temperature for 18 hours. The solvent is distilled off under reduced pressure, the residue washed several times with 10% aqueous sodium bicarbonate and water, dried under vacuum and crystallized from benzene to give 9-(2'-acetoxyethylamino)-7-methoxy-4-methyl-1-nitroacridine (82% yield), m.p. 145-148° C., anal. $C_{19}H_{19}N_3O_5Cl$ (C, H, N). $^1$H NMR ($d_6$DMSO): δ 1.6(t, 3H, H-2'), 2.6(s, 3H, CH3), 3.4(s, 4H, H-2', H-1'), 4.0(s, 3H, $CH_3$), 7.66(dd, 1H, $J_1$=9.3 Hz, $J_2$=2.5 Hz, H-6), 7.85(d, 1H, J=8.2 Hz, H-3), 8.00(s, 1H, H-8), 7.7(t, 1H, H-6), 8.15(d, 1H, J=7.8 Hz, H-2), 8.20(d, 1H, J=7.8 Hz, H-5).

1-Nitroacridine/antiangiogenic Compositions

1-Nitro-9-Hydroxyethylaminoacridine+Combretastatin

In the example, the concerted action of 1-nitro-9-hydroxyethylaminoacridine with an antiangiogenic agent combretastatin is described.

Materials and Methods

Dunning G and MAT-LyLu cells are used. Dunning G cells are non-metastatic tumor producing prostate cancer cells derived from spontaneous tumors from Copenhagen rats. MAT-LyLu is a metastatic variant of Dunning G cells that is a very aggressive cell line. 10,000 MAT-LyLu cells implanted into syngeneic animals produces tumors in 2-3 weeks. Both cell lines are grown in culture. In vivo experiments with MAT-LyLu cells are presented.

Growth of Cancer Cells in Culture

Dunning G and MAT-LyLu cells (Yedavelli et al, 1999, Int. J. Mol. Med. 4:243-248) are grown in RPMI 1640 containing 10% fetal bovine serum (FBS) supplemented with penicillin (50 IU/mL), streptomycin (50 μg/mL), 2 mM L-glutamine and 2.5 mM dexamethasone. Cells are fed twice a week and are trypsinized with 0.05% trypsin-EDTA at eighty to ninety percent cell confluency. Since the cells are rapidly growing, care is taken that the cells do not reach hundred percent confluency. Cells injected for growth in Copenhagen rats are generally taken from flasks that are between and fifty and seventy five percent confluent. MAT-LyLu cells are washed twice with phosphate buffered saline (PBS) and then trypsinized and suspended in PBS at a concentration of 100,000 cells per mL. Each animal is injected with 0.1 mL of cell suspension with an effective dose of 10,000 live MAT-LyLu cells or one million Dunning G cells per rat. Cell viability is always determined by the trypan blue exclusion test and samples that exhibited less than 98% viability are discarded. Cells are injected into the right flank of the animal that have been shaved prior to the injection. All injections are intradermal (i.d.), using an insulin syringe. Cells are kept at 4 degrees C. at all times prior to injections. All experimental groups and the control animals are injected at the same time with the same batch of cells.

Animal Experiments

Four to five week old Copenhagen rats are purchased from Harlan Sprague Dawley, Indianapolis, Ind., and allowed to acclimate for one week, feeding on Purina 5001 rat chow. At the end of one week, the rats are randomized into different experimental groups. Body weights of the animals measured twice a week. Live MAT-LyLu (10,000 cells/rat) are injected in all animals. Animals are injected i.p twice a week with 1-nitro-9-hydroxyethylaminoacridine (0.6 mg/kg body weight), mitoxantrone (0.6 mg/kg body weight), combretastatin (10 mg/kg body weight). Treatment is started on day eighteen for animals injected with MAT-LyLu and day 25 for animals injected with Dunning G cells. All animals are housed in hanging cages with three/four animals per cage and had ad libitum access to food and drinking water and are kept on twelve-hour diurnal cycle. All injections and tumor measurements are performed under light anesthesia (metofane inhalation). Experimental end point measurements include body weight, tumor incidence, rate of tumor growth, number of animals with pulmonary metastases and number of visible metastatic nodules per lung of the tumor bearing animal and histopathological examination of the tumors. Tumor diameter is measured using vernier calipers and tumors are fixed in formalin. The experiment is terminated when the tumor size in the control animals is 3 cms diameter. Sacrifice of the animals is done by carbon dioxide asphyxiation. The experiments described with MAT-LyLu, a variant of the Dunning G cell line that metastasizes to the lymph node and lung when implanted in syngeneic Copenhagen rats.

Preparation of Stock Solution of Drugs for in vitro and in vivo Studies

Stock solution 1-nitro-9-hydroxyethylaminoacridine is made in dimethylsulfoxide at 4.2 mg/mL. The mitoxantrone used is Novantrone 25 mg/12.5 mL (Immunex, Seattle, Wash.) containing inactive ingredients sodium chloride 0.8% w/v, sodium acetate 0.005% w/v, and acetic acid 0.046% w/v. Combretastatin is water soluble and is dissolved at a concentration of 10 mg/mL/kg body weight All drugs for injection in animals are diluted in PBS such that the total volume injected is between 0.1 to 0.2 mL.

Results

Growth of MAT-LyLu cells in Copenhagen rats is very rapid and the cells readily metastasize to the lung and lymph nodes. The anti-tumor activity of 1-nitro-9-hydroxyethylaminoacridine in combination with combretastatin on tumor incidence, tumor growth and pulmonary metastasis of MAT-LyLu induced tumor cell growth is examined.

Tumors are initiated by injecting 10,000 live cells intradermally on the right flank of the animal. Predictably, tumors reach a palpable size in these rats at the end of fourteen to twenty days after which there is an exponential growth.

Figure 2:
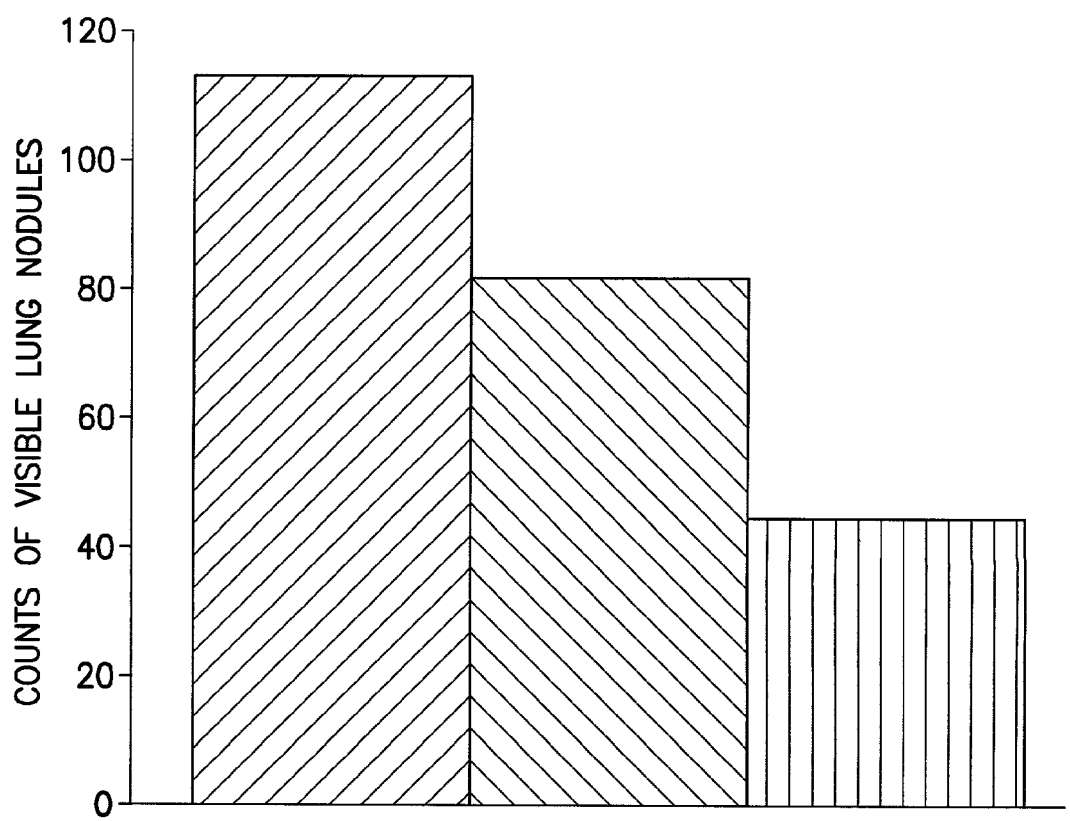
FIG. 2 shows the reduction in pulmonary metastases by 1-nitro-9-hydroxyethylaminoacridine+antiangiogenic agent, combretastatin as measured by counts of visible lung nodules. ■Control, ▧mitroxantrone+combretastatin, ▢combretastatin+1-nitro-9-hydroxyethylaminoacridine. Animals are treated with the same dosages as above.

The results obtained are shown in FIGS. 1 and 2. It is evident in FIG. 1 that the combination of 1-nitro-9-hydroxyethylaminoacridine (0.6 mg/kg) and combretastatin (10 mg/kg) produces a very significant antitumor effect producing a reduction in tumor diameter by almost 90%.

Combinations of 1-nitro-9-hydroxyethylaminoacridine and combretastatin did not show any overt toxicity and the doses administered are well tolerated. The only toxicity visible is an occasional diarrhea in about ten to twenty percent of the animals.

The effect of the two drugs, mitoxantrone and 1-nitro-9-hydroxyethylaminoacridine in combination with the antangiogenic agent combrestastatin is very significant in the reduction of the number of lung nodules. Combretastatin and 1-nitro-9-hydroxyethylaminoacridine show a statistically significant (P=0.05) reduction in lung nodules as compared to control as well as MITX+combretastatin.

Both FIGS. 1 and 2 suggest that the use of 1-nitro-9-hydroxyethylaminoacridine with an antiangiogenic agent can have a profound effect on the primary as well as metastatic tumors.

9-(2'-Hydroxyethylamino)-4-methyl-1-nitroacridine+ Pancratistatin

Results of studies of 9-(2'-hydroxyethylamino)-4-methyl-1-nitroacridine+with an antiangiogenic agent pancratistatin is described.

Materials and Methods

Growth of Cancer Cells in Culture

In these studies, TSU cells are used. TSU cells are human prostate cancer cells (Iizumi et al., 1987, J. Urol. 137:1304-1306). TSU cells are grown in RPMI-1640 medium supplemented with 10% fetal bovine serum and the antibiotics penicillin (50 IU/ml), streptomycin (50 μg/ml) and 2 mM L-glutamine. Cells are fed with fresh media twice a week and are trypsinized using 0.05% trypsin-EDTA. Cells used for injection are always in the log phase of their growth (70-80%) confluent flask and cell viability is checked by trypan-blue exclusion test prior to injection. Only cells >95% confluent are used. In a typical experiment, TSU cells are suspended at a concentration of $20\times10^6$/ml and 0.1 ml is injected subcutaneously into the right flank of Balb/c, nu/nu mice.

Preparation of Stock Solution of Drugs for in vitro and in vivo Studies

Stock solution 9-(2'-hydroxyethylamino)-4-methyl-1-nitroacridine is made in DMSO at 0.16 mg/mL. Pancratistatin is made in distilled water and is dissolved at a concentration of 1 mg/mL. All drugs for injection in animals are diluted in PBS such that the total volume injected is about 0.1 mL.

Animal Experiments

Six week old Balb/c nu/nu mice are obtained from the Jackson Laboratories, Bar Harbor, Me. The animals are allowed to acclimate for 2-3 weeks and kept in separate cages with controlled air filtration. They are fed regular rodent chow and are randomized into different experimental groups. One group is the control group injected intraperitoneally with solvents in which the drugs are dissolved. In the case where one of the solvents is distilled water and the other is DMSO, the control animals are injected with DMSO, 0.1 ml intraperitoneally. $2\times10^6$ TSU cells are injected subcutaneously into the right flank and the animals are monitored daily for tumor formation. Palpable tumors are obtained 7-10 days after injection of the tumor cells. Tumor diameter is measured using vernier calipers in animals under light anesthesia. Treatment with 9-(2'-hydroxyethylamino)-4-methyl-1-nitroacridine (0.6 mg/kg) and pancratistatin (5.0 mg/kg) is started when the tumors are roughly 0.6 cm in diameter and the drugs are administered by intraperitoneal injection twice a week for three weeks.

Results

Figure 3:
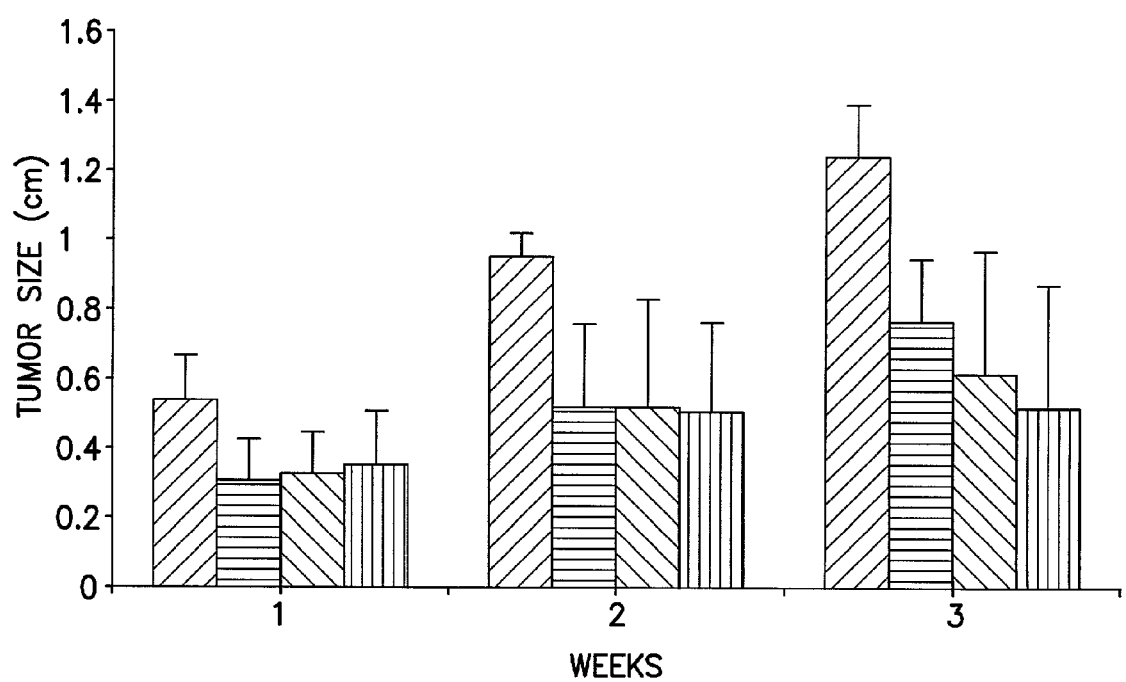
FIG. 3 shows the effect of 9-(2'-hydroxyethylamino)-4-methyl-1-nitroacridine+pancratistatin on the growth of human prostate cancer cell line, TSU in Balb/c/nu/nu mice. ▢Control, ▤9-(2'-hydroxyethylamino)-4-methyl-1-nitroacridine, ▨pancratistatin, ▥9-(2'-hydroxyethylamino)-4- methyl-1-nitroacridine+pancratistatin. Five animals/group are randomized in this study. Tumors are initiated by subcutaneous injection of $2\times10^6$ live TSU cells and treatment is started seven days after the tumor is palpable (about 0.5 cm). Treatment is carried out at a concentration of 9-(2'-hydroxyethylamino)-4-methyl-1-nitroacridine (0.6 mg/kg) and pancratistatin (5 mg/kg) twice a week for three weeks.

FIG. 3 shows the effect of the combination of 9-(2'-hydroxyethylamino)-4-methyl-1-nitroacridine (0.6 mg/kg) and pancratistatin (5.0 mg/kg) on the growth of the human prostate cancer cell line, TSU in Balb/c/nu/nu. This combination appears to have significant tumor inhibitory effect on the growth of tumor prostate cancer cells.

The specific embodiments herein disclosed are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A composition comprising at least one 1-nitroacridine, wherein said 1-nitroacridine is selected from the group consisting of 1-nitro-4-alkyl-9-hydroxyalkylaminoacridine, 1-nitro-4-alkoxy-9-hydroxyalkylaminoacridine, 1-nitro-9-alkoxyalkylaminoacridine and 1-nitro-9-alkylcarboxyalkylaminoacridine and at least one antiangiogenic substance.

2. The composition according to claim 1, wherein the antiangiogenic substance is selected from the group consisting of angiostatin, endostatin, pancratistatin, phenstatin and combretastatin.

3. The composition according to claim 1, wherein said 1-nitroacridine is a 1-nitro-4-alkyl-9-hydroxyalklylaminoacridine, wherein said 1-nitro-4-alkyl-9-hydroxyalklylaminoacridine is selected from the group consisting of 1-nitro-4-methyl-9-hydroxyalklylaminoacridine and 1-nitro-4-alkyl-9-hydroxyethylaminoacridine, and wherein said 1-nitroacridine is a 1-nitro-4-alkoxy-9-hydroxyalklylaminoacridine, wherein said 1-nitro-4-alkoxy-9-hydroxyalklylaminoacridine is selected from the group consisting of 1-nitro-4-methoxy-9-hydroxyalklylaminoacridine and 1-nitro-4-ethoxy-9-hydroxyethylaminoacridine.

4. A composition comprising at least one 1-nitroacridine, wherein said 1-nitroacridine is selected from the group consisting of 1-nitro-4-alkyl-9-hydroxyalkylaminoacridine, 1-nitro-4-alkyl-9-hydroxyalkylaminoacridine, 1-nitro-9-alkoxyalkylaminoacridine and 1-nitro-9-alkylcarboxyalkylaminoacridine and at least one substance that inhibits tumor vasculature or biochemical processes that affect new blood vessel growth.

5. A composition comprising (a) at least one 1-nitroacridine selected from the group consisting of 1-nitro-4-alkyl-9-hydroxyalkylaminoacridine, 1-nitro-4-alkoxy-9-hydroxyalkylaminoacridine, 1-nitro-9-alkylcarboxyalkylaminoacridine and 1-nitro-9-alkoxyalkylaminoacridine and (b) at least one tumor inhibitor substance selected from the group consisting of an antiangiogenic substance, a nucleic acid synthesis inhibitor and a cell cycle inhibitor.

6. A composition comprising (a) at least one 1-nitroacridine elected from the group consisting of 9-(2'-hydroxyethylamino)-4-methyl-1-nitroacridine, 9-(2'-hydroxyethylamino)-7-methoxy-1-nitroacridine, 9-(2'-hydroxyethylamino)-7-methoxy-4-methyl-1-nitroacridine, 9-(2'-acetoxyethylamino)-1-nitroacridine, 9-(2'-propionoxyethylamino)-1-nitroacridine, 9-(3'-hydroxypropylamino)-7-methoxy-1-nitroacridine, 9-(3'-hydroxypropylamino)-4-methyl-1-nitroacridine, 9-(2'-acetoxyethylamino)-4-methyl-1-nitroacridine 9-(2'-propionoxyethylamino)-4-methyl-1-nitroacridine, 9-(3'-acetoxypropylamino)-4-methyl-1-nitroacridine, 9-(2'-propionoxypropylamino)-4-methyl-1-nitroacridine, 9- (2'-hydroxyethylamino)-4-methoxy-1-nitroacridine, 9-(3'-hydroxypropylamino)-4-methoxy-1-nitroacridine, 9-(4'-hydroxybutylamino)-4-methoxy-1-nitroacridine, 9-(4'-hydroxybutylamino)-7-methoxy-1-nitroacridine and 9-(2'-acetoxyethylamino)-7-methoxy-4-methyl-1-nitroacridine and (b) at least one tumor inhibitor substance selected from the group consisting of a nucleic acid synthesis inhibitor, a cell cycle inhibitor and an anti-angiogenic substance.

7. A method for inhibiting tumor growth in a mammal comprising administering to said mammal an amount of the composition of claim 1 effective to inhibit tumor growth.

8. A method for inhibiting metastases in a mammal comprising administering to said mammal an amount of the composition of claim 1 effective to inhibit metastases.

9. A method for inhibiting tumor growth in a mammal comprising administering to said mammal an amount of the composition of claim 5 effective to inhibit tumor growth.

10. A method for inhibiting metastases in a mammal comprising administering to said mammal an amount of the composition of claim 5 effective to inhibit metastases.

11. A method for inhibiting tumor growth in a mammal comprising administering to said mammal at least 1-nitroacridine, wherein said 1-nitroacridine is selected from the group consisting of 1-nitro-4-alkyl-9-hydroxyalkylaminoacridine, 1-nitro-4-alkyl-9-hydroxyalkylaminoacridine, 1-nitro-9-alkoxyalkylaminoacridine and 1-nitro-9-alkylcarboxyalkylaminoacridine and at least one antiangiogenic substance, wherein the combination of 1-nitroacridine and antiangiogenic substance is an amount effective to inhibit tumor growth.

12. The method according to claim 11, in which the tumor is selected from the group consisting of breast cancer, prostate cancer, colon cancer, and leukemia.

13. The method according to claim 11, wherein the tumor is a prostate tumor.

14. The method according to claim 11, wherein the tumor is selected from the group consisting of carcinoma, lymphoma and sarcoma.

15. A method for inhibiting tumor growth in a mammal comprising administering to said mammal an amount of the composition of claim 6 effective to inhibit tumor growth.

16. A method for inhibiting metastases in a mammal comprising administering to said mammal an amount of the composition of claim 6 effective to inhibit metastases.

17. A method for inhibiting tumor growth in a mammal comprising administering to said mammal at least 1-nitroacridine, wherein said 1-nitroacridine is selected from the group consisting of 1-nitro-4-alkyl-9-hydroxyalkylaminoacridine, 1-nitro-4-alkoxy-9-hydroxyalkylaminoacridine, 1-nitro-9-alkoxyalkylaminoacridine and 1-nitro-9-alkylcarboxyalkylaminoacridine and at least one antiangiogenic substance, wherein the combination of 1-nitroacridine and antiangiogenic substance is an amount effective to inhibit metastases.

18. A method for inhibiting tumor growth in a mammal comprising administering to said mammal at least one 1-nitroacridine selected from the group consisting of 1-nitro-4-alkyl-9-hydroxyalkylaminoacridine, 1-nitro-4-alkyl-9-hydroxyalkylaminoacridine, 1-nitro-9-akoxyalkylaminoacridine and 1-nitro-9-alkylcarboxyalkylaminoacridine and at least one tumor inhibitor substance, wherein the tumor inhibitor substance is selected from the group consisting of an antiangiogenic substance, a nucleic acid synthesis inhibitor and a cell cycle inhibitor, wherein the combination of 1-nitroacridine and tumor inhibitor substance is an amount effective to inhibit tumor growth.

19. A method for inhibiting metastases in a mammal comprising administering to said mammal at least one 1-nitroacridine selected from the group consisting of 1-nitro-4-alkyl-9-hydroxyalkylaminoacridine, 1-nitro-4-alkyl-9-hydroxyalkylaminoacridine, 1-nitro-9-alkoxyalkylaminoacridine and 1-nitro-9-alkylcarboxyalkylaminoacridine derivative and at least one tumor inhibitor substance, wherein the tumor inhibitor substance is selected from the group consisting of an antiangiogenic substance, a nucleic acid synthesis inhibitor and a cell cycle inhibitor, wherein the combination of 1-nitroacridine and tumor inhibitor substance is an amount effective to inhibit metastases.

20. The method according to claim 19, in which the mammal is a human patient.

21. A method for inhibiting prostate tumor growth in a mammal comprising administering to said mammal a 1-nitroacridine selected from the group consisting of 1-nitro-4-alkyl-9-hydroxyalkylaminoacridine, 1-nitro-4-alkyl-9-hydroxyalkylaminoacridine, 1-nitro-9-alkylcarboxyalkylaminoacridine and 1-nitro-9-alkoxyalkylaminoacridine and a tumor inhibitor substance wherein the tumor inhibitor substance is selected from the group consisting of an antiangiogenic substance, a nucleic acid synthesis inhibitor and a cell cycle inhibitor, wherein the combination of 1-nitroacridine and tumor inhibitor substance is an amount effective to inhibit or prevent said prostate tumor growth.

* * * * *